United States Patent [19] [11] 4,198,433
Golovinski et al. [45] Apr. 15, 1980

[54] ANTI-TRANSPLANTED TUMOR REMEDY

[75] Inventors: Evgeni V. Golovinski; Boris V. Alexiev; Alexander V. Spassov; Stoycho B. Stoev; Lilyana S. Maneva; Emanuil A. Emanuilov; Tzanko S. Stoychev; Ivan I. Angelov, all of Sofia, Bulgaria

[73] Assignee: Ecnpk Po Biologia I Mediko-Biologichni Problemi Pri Ban, Sofia, Bulgaria

[21] Appl. No.: 808,598

[22] Filed: Jun. 21, 1977

Related U.S. Application Data

[63] Continuation-in-part of Ser. No. 654,255, Feb. 2, 1976, abandoned.

[51] Int. Cl.² .............................................. A61K 31/16

[52] U.S. Cl. ................................................... 424/320
[58] Field of Search ................ 424/320, 311, 226, 324

[56] References Cited

U.S. PATENT DOCUMENTS 3,897,494   7/1975   Alexiev et al. ...................... 424/319

*Primary Examiner*—Jerome D. Goldberg
*Attorney, Agent, or Firm*—E. Janet Berry; Lawrence Rosen

[57] ABSTRACT

The invention is a composition for treatment of transplanted tumors in animals which is a mixture of the hydrogen bromide salts of bis-(beta-dichloroethyl)-hydrazides of cystine and cysteine, method of preparation therefor, and use thereof for treatment of transplanted tumors in animals.

3 Claims, No Drawings

ANTI-TRANSPLANTED TUMOR REMEDY

This application is a continuation-in-part of copending patent application Ser. No. 654,255, filed Feb. 2, 1976 and now abandoned.

It is a purpose of this invention to create a cytostatic composition for treatment of transplanted tumors in animals by structurally combining antimetabolics (the hydrazide of cystine and of cysteine, respectively) with an alkylating group. In connection with the invention, U.S. Pat. No. 3,897,494, its specification and claims, are referred to as relevant.

The invention itself relates to the contents and the anti-tumor effect of treatment of transplanted tumors in animals of a synthetic cytostatic composition from the group of the modified natural alpha-amino acids based on cystine and cysteine, connected by a hydrazide linkage with bis-(betachloroethyl)-hydrazine. The anti-tumor remedy for treatment of transplanted tumors in animals is a combination of bromo-hydrogenic salts of L-cystinyl-bis-[(N,N-beta-chloroethyl)hydrazine]. (I) and L-cysteinyl(N,N-beta-chloroethyl)hydrazide (II).

The obtaining of (N,N-β-chloroethyl) hydrazides of cystine and cysteine is carried out by the interaction between the acid chloride of the benzyloxycarbonyl-L-cystine and the asymmetrical (N,N-β-chlorethyl) hydrazine in a medium of ethyl acetate with further deblocking of the thus obtained benzyloxycarbonyl-cystine-bis (N,N-β-chloroethyl/hydrazide) by treating it with a hydrogen bromide solution in glacial acetic acid. The reactions are carried out according to the following equation:

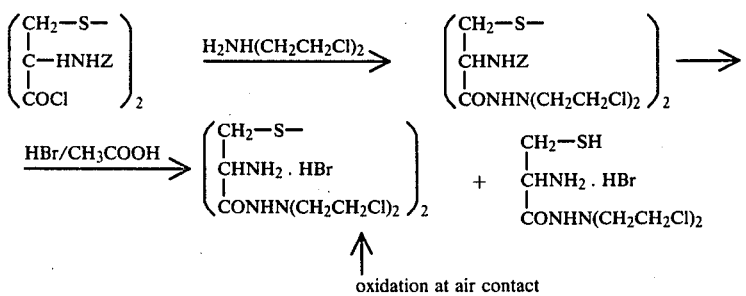

wherein Z=OCOCH$_2$C$_6$H$_5$.

The detailed description of the synthesis of (N,N-β-chloroethyl/hydrazides) of cystine and cysteine is given in U.S. Pat. No. 3,897,494.

The composition of the mixture can vary from 1 to 99 mole percent for each of the components. The optimum conditions for obtaining the anti-tumor remedy for transplanted tumors in animals require the components I and II in the mixture to be present in the ratio of 95:5 mole percent.

The remedy, according to the invention, takes the form of colourless hygroscopic crystals, highly soluble in water and very little soluble in organic solvents. The substance is D-active. The elementary analysis and the molecular weight as defined by the mass-spectrograph are well coordinated with the ingredients mentioned above. The infrared spectrum contains absorbing lines of a sulfhydryl band. Furthermore, the remedy has a positive reaction for the sulfhydryl groups with Elman's reagent, which precipitates evidently due to oxidation when air is passed for a short time through the solution. This makes it possible for both forms to be colorimetrically defined when reducing and preserving the substance. When exposed to air for a longer time the remedy disintegrates, becoming darker and emitting a sharp smell. If stored under a nitrogen atmosphere and in a tightly closed container this change does not occur.

Microbiological pre-screening has indicated that the preparation has bacteriostatic action. It impedes the growth of the staphylococcal mutants UF-2 and UF-3 and of Sarcina lutea. It proved to be non-active towards other microorganisms. The cancerostatic activity has been tested on transplantable tumors in mice and rats. The water solution of the anti-tumor remedy in a volume of 1 ml. is injected intraperitoneally with cases of solid transplantable tumors and subcutaneously with cases of ascitic tumors. The control animals are treated in the same way with physiological solution. Each test requires 6 experimental animals and 6 control animals. The treatments start at the 4-5th day after the tumor transplantation. Until the animals die (one day after suspending the treatment) when the treatment results are to be determined, not a single death has been recorded. The difference in survival between the experimental and the control animals are statistically reliable when the treatment is performed according to the method of Student-Fisher-Moshkovski.

The essence of the invention is the composition and antitumor effect on transplantable tumors in animals of a synthetic cytostatic agent from the group modified natural L-amino acids and is based on cystine and cysteine combined in a hydrazide with bis-(β-chloroethyl) hydrazine.

The product which has been tested is a mixture of hydrogen bromides of L-cystinyl-bis[N,N-β-chloroethyl (hydrozide)] (I) and L-cysteinyl-bis[N,N-β-chloroethyl (hydrazide)] (II). The content of the mixture can vary from 1 to 99 moles percent for each of the components. Under the optimum conditions for the production of the antitumor agent for transplantable tumors in animals, the correlation between the components I and II in the mixture is 95:5 mole percent.

The antitumor product having the composition of I:II=95:5 mole percent has been examined for its cancerostatic effect on transplanted tumors in mice and rats. With respect to the Myeloma P-8, Walker's carcinosarcoma, Joshida's sarcoma and the Lynphosarcoma of Pliss, the suppression of the transplantable tumor growth was 100 percent in doses of 12 mg per kg, 10 mg per kg, 5 mg per kg and 10 mg per kg, respectively, applied during 8, 8, 10 and 10 consecutive days respectively. Regarding the Jensen's sarcoma it was 80 percent in dosage 5 mg per kg applied for 10 days. With respect to the ascitic tumors of Ehrlich and Gerens suppression of the transplantable tumor growth was not established.

The following Examples are presented to further explain and exemplify the invention and to show both the effectiveness and safety for use of the remedy.

EXAMPLE I

Data for the Effectiveness of the Preparation (Antitumor effect of the preparation)

TABLE 1

| Transplanted Tumor | Dosage mg/kg | Administration | Mode of administration | Percentage of suppression |
|---|---|---|---|---|
| Joshida's Sarcoma | 5 | 10 consecutive days | per os | 100 |
| Walker's carcinosarcoma | 5 | 10 consecutive days | per os | 77 |
| Joshida's Sarcoma | 2 | 10 times every second | intraperitoneally | 75 |
| Walker's carcinosarcoma | 2 | 10 times every second | intraperitoneally | 100 |

It is noteworthy that the effect of the preparation is preserved even in the peroral administration.

EXAMPLE II

Data for the Safety of the Preparation (Toxicity of the preparation)

A. Examples of acute toxicity (with supplements).

TABLE 2

| Mode of Administration | Animals | |
|---|---|---|
| | Mice | Rats |
| Intraperitoneally | 71 | 47 |
| Subcutaneous | 76 | — |
| Per os | — | 75 |
| Intravenous | 72 | — |

B. Toxicity of the preparation after 7 days intravenous administration on rabbits.

The toxic effect of the preparation administered intravenously each day in the course of 7 days on rabbits with 2,200 gr mean body weight has been studied. The mortality, changes in the body weight, changes in the blood picture, changes in the serum transaminases (determined with the Boeringer's tests) and histomorphological alterations have been traced.

All the rabbits injected intravenously with 5 mg per kg of the preparation every day in the course of 7 days survived the treatment. Their body weight from 2125±95.5 gr mean values decreased slightly (statistically insignificant) to 2046±165.7 gr. The changes in the blood indices are shown in Table 3.

TABLE 3

Changes in the blood indices after 7 days Treatment with 5 mg per kg of the Preparation

| Index | Preliminary | After the 8th day | Degree of significance |
|---|---|---|---|
| Leucocytes | 8100 ± 831 | 3960 ± 757 | P ≦ 0.01 |
| Erythrocytes | 5667000 ± 130800 | 4112000 ± 398500 | P ≦ 0.01 |
| Haemoglobin (after Sahli) | 88.8 ± 2.7 (in percentage) | 69.8 ± 2.2 (in percentage) | P ≦ 0.001 |
| Hematocrit values | 42 ± 2.6 | 37 ± 0.6 | P ≦ 0.1 |

It can be seen from Table 3, that in a 7 day treatment of rabbits with the preparation, the number of the leucocytes diminishes considerably i.e. 51 percent. Also considerable and significant is the decrease of the erythrocytes, 36 percent, and of the haemoglobin (after Sahli) by 21 percent. The decrease of the hematocrit values is considerably less and insignificant, about 12 percent.

The changes in the activity of serum glutamic pyruvic transaminase (SGPT) and serum glutamic oxalacetic transaminase (SCOT) after 7 days treatment of rabbits with 5 mg per kg of the preparation intravenously are shown on Table 4.

TABLE 4

Changes in SGPT and SGOT in mU/lml serum

| Enzymes | Preliminary | On the 8th day | Degree of significance |
|---|---|---|---|
| SGPT | 16.3 ± 2.14 | 13.8 ± 3.16 | insignificant |
| SGOT | 16.9 ± 2.04 | 8.8 ± 1.99 | P ≦ 0.002 |

The serum glutamic oxalacetic transaminase diminishes considerably and significantly after 7 days treatment with the preparation (by 48 percent) while the decrease of the activity of the serum glutamic pyruvic transaminase is 15 percent and is insignificant.

Usually the damage of the hepatic cells is associated with an increase of the activity of SGOT and SGPT. The decrease of the activity of the transaminase under the effect of the preparation is believed to be due to the suppression of the biosynthesis of these enzymes.

Three of the rabbits treated intravenously with 5 mg per kg of the preparation have been left alive till the 15th day, in order to trace the alterations in the examined indices one week after the discontinuance of the administration of the preparation. The mean values of these indices for the three rabits are shown in Table 5.

TABLE 5

Mean values for the alterations in the body weight, the blood picture and the transaminase activity

| Index | Measure | Preliminary | 8th day | 15th day |
|---|---|---|---|---|
| Body Weight | gr | 2130 | 1883 | 2050 |
| Leucocytes | No | 7267 | 3633 | 5283 |
| Erythrocytes | No | 5600000 | 4613000 | 4847000 |
| Haemoglobin after Sahli | Percentage | 90 | 69 | 69 |
| SGPT | mU/lml | 15.1 | 10.8 | 17.4 |
| SGOT | mu/lml | 16.7 | 6.9 | 11.4 |
| Hematocrit values | — | 43 | 37 | 34 |

The data demonstrate that the changes occurring in the body weight, the blood picture and the transaminase activity of rabbits injected with 5 mg per kg of the preparation are reversible and the rabbits begin to recover after the discontinuance of the treatment. More rapid and more marked is the restoration of the number of the leucocytes in comparison with that of the erythrocytes. The activity of SGOT is suppressed to a greater degree by the preparation and is restored more slowly in comparison with that of SGPT.

C. Toxicity of the preparation after 30 days intraperitoneal administration in rats Alterations in the blood picture of rats treated intraperitoneally every day for 30 days with 5 mg/kg of the preparation

TABLE 6

| Index | Preliminary | 15th day | 30th day | Degree of Significance |
|---|---|---|---|---|
| Leucocytes | 5815 ± 164 | 4355 ± 120 | 4825 ± 70 | $P \leq 0.001$ |
| Erythrocytes | 6920000 ± 113800 | 6480000 ± 166500 | 4180000 ± 624000 | $P \leq 0.001$ |
| Haemoglobin | 110 ± 0.7 | 79.6 ± 1.2 | 72 ± 0.9 | $P \leq 0.001$ |
| Hematocrit values | 46 ± 0.7 | 38 ± 0.4 | 36 ± 0.5 | $P \leq 0.001$ |

The data show that in daily intraperitoneal treatment of rats with 5 mg of preparation per kg a significant decrease of the number of the leucocytes, haemoglobin and hematocrit values occurs as early as the 15th day. In the continuation of the treatment to the 30th day, a further statistically significant decrease of the number of the erythrocytes and the haemoglobin and hematocrit values is observed. Particularly noteworthy is the decrease in the number of erythrocytes during the second half of the treatment. It is worth mentioning that in the given experiment the number of leucocytes is even slightly increased on the 30th day in comparison with that on the 15th day, although the administration of the preparation has been continued.

In the control group (rats treated intraperitoneally with physiological salt solution every day in the course of 30 days) changes in the blood picture have not been established.

TABLE 7

| | Blood picture of the control group rats | | |
|---|---|---|---|
| Index | Preliminary | 15th day | 30th day |
| Leucocytes | 5565 ± 141 | 5575 ± 103 | 5765 ± 74 |
| Erythrocytes | 6792000 ± 169000 | 6825000 ± 116500 | 6830000 ± 75400 |
| Haemoglobin | 106 ± 0.9 | 106 ± 0.4 | 107 ± 0.4 |
| Hematocrit values | 46 ± 0.6 | 46 ± 0.4 | 48 ± 0.4 |

D. Toxicity of the preparation after three months administration.

The toxicity of the preparation administered intraperitoneally in the course of three months in doses 2, 4 and 8 mg per kg to 80 white male rats with mean body weight of 120 gr has been studied. The mortality, the changes in the body weight and in the blood picture at the end of the experiment and the histopathological alterations in the viscera have been traced.

The animals treated with 8 mg per kg dose of the preparation died between the 17th and the 37th day from the beginning of the treatment, and in the last few days before the death they showed a marked decrease of their body weight-from 120 to 75 gr on an average. The two groups of rats treated with 2 and 4 mg per kg showed no fatal cases during the three months period of the treatment. The initial mean body weight of the animals was 120 gr. On the 90th day the mean body weight of the animals treated with 2 mg. per kg. was 170 gr.; of these treated with 4 mg. per kg. it was 162 gr and of the control animals the mean body weight was 180 gr. These facts demonstrate that the preparation administered in the course of three months in 2 and 4 mg. per kg. doses does not inhibit particularly the natural increase of the animals' body weight. The changes in the blood picture at the end of the experiment are shown on Table 8.

TABLE 8

| | Blood picture at the end of the experiment | | |
|---|---|---|---|
| Indices | Controls | Treated with 2 mg/kg | Treated with 4 mg/kg |
| Haemoglobin | 106 ± 8 | 75 ± 9 | 63 ± 10 |
| Erythrocytes | | $\cdot 10^5 \pm 2, 3 \cdot 10^5$ | $2, 4 \cdot 10^5 \pm 614\,820$ |
| Leucocytes | 6200 ± 1100 | 3050 ± 980 | 2500 ± 420 |
| Hematocrit values | 43 ± 3.5 | 40 ± 2.8 | 45 ± 3 |
| Coagulation in seconds | 120 ± 15 | 50 ± 4.8 | 40 ± 4.2 |

The data show that the preparation in 2 and 4 mg. per kg. doses administered in the course of three months suppresses to a considerable degree both the erythropoiesis and the leucopoiesis.

In these experiments the following histomorphological alterations have been established: with 4 mg per kg dose a decrease of the RNA in the cells, lymphocytes grouping in some places and pyroninophilia have been observed in the liver. In that dosage a several fold increase of the plasmatic cells in the lamina propria of the intestines have also been observed. There were no changes in the remaining organs. With 2 mg per kg dose no deviations from the normal structure of the organs have been established.

E. Studies for a local irritating and local anaesthetic effect of the preparation.

On three male rabbits from the Chinchilla breed, 5–6 drops from the 10 percent solution of the preparation have been dropped in their left eye. in the right eye, the same quantity of the solvent-the physiological salt solution-has been dropped. The effect of the preparation was registered according to the reaction of the conjunctiva. Slight tears appeared at the 5th-10th minute. Other changes have not been observed. There were no changes at the 24th hour.

The preparation has no local irritating effect.

On three male rabbits from the Chinchilla breed, 5–6 drops from the 10 percent solution of the perparation have been dropped in their left eye. In the right eye, the same quantity of the solvent-the physiological salt solution-has been dropped. The presence of a blinking reflex in touching the conjunctiva with a hair has been registered.

| | Experimental (left) eye | Experimental (right) eye |
|---|---|---|
| 1st minute | reacts | reacts |
| 5th minute | reacts | reacts |
| 10th minute | reacts | reacts |
| 30th minute | reacts | reacts |
| 24th hour | reacts | reacts |

In touching, the reaction of both eyes is equal. The preparation has no local anaesthetic effect.

EXAMPLE III

Some examples of the anti-tumor effect

| Transplanted Tumor | Dose ml/kg | Application on days in order | % of Suppression |
|---|---|---|---|
| 1. Myeloma P-8 | 12 | 8 | 100 |
| 2. Crocker's sarcoma 180 | 10 | 10 | 80 |
| 3. Walker's Carcinosarcoma | 10 | 8 | 100 |
| 4. Pliss's Lymphosarcoma | 5 | 9 | 60 |
|  | 10 | 10 | 100 |
| 5. Joshida's sarcoma | 5 | 10 | 100 |
| 6. Jensen's sarcoma | 5 | 10 | 75 |
| 7. Erlich's and Guerin's ascitic tumors | 5 |  | no suppression |

The animals left to survival for 120 days; 5 survived without traces of tumor issue; 1 died on the 35th day from receiving transplant; all control animals died between the 18th and the 26th day.

EXAMPLE IV

Examples for Acute Toxicity

| $LD_{50}$ in mg/kg | Mice | Rats |
|---|---|---|
| Intraperitoneal introduction | 71 | 47 |
| Subcutaneous Introduction | 76 | — |

EXAMPLE V

Example for Subacute Toxicity

A group of 20 rats injected for 30 days with 5 mg/kg intraperitoneally.

|  | On the 15th day | On the 30th | Controls |
|---|---|---|---|
| Haemoglobin % | 80 | 71 | 108 |
| Erythrocytes | 6540000 | 4180000 | 6780000 |
| Leucocytes | 4350 | 4880 | 5800 |

The pharmacological characteristics of the remedy include testing the effect of the preparation on the blood pressure, pulse and breathing. The test was performed on 5 male cats drugged with urethane, their blood pressure being registered after the method of Ludwig-Zion and their breathing-with Marreev's capsule. The remedy was introduced intravenously in doses of 10,50 and 100 mg/kg. every hour. Under this test condition the remedy lowers the blood pessure which is limited by the speed of introduction and not by the total quantity of the preparation. The remedy does not considerably influence the pulse but there is excited breathing at the start of the experiment, until at the end of experiment the breathing gradually slows down and its amplitude diminishes. All these changes reflect a comparatively slowly developing toxic effect.

To explain some mechanisms of the cytostatic effect of the preparation experiments has been carried out to show its influence on the biosynthesis of the DNA in tumor cells of Erlich's ascitic tumor. An inhibiting effect of up to 80% has been established. The cytostatic activity of the remedy corresponds to its chemical composition because the remedy it an antimethabolite of the amine acid (cystine/cysteine) combined with the alkylating effect due to the bis-(chlorethyl) hydrazine remnants in the molecule. The alkylating effect of the remedy is proved by means of a positive paranitro-benzyl-pyridine reaction which it produces. It is more clearly expressed than that of the sarcolysine.

What is claimed is:

1. A composition adapted for treatment of transplanted tumors comprising a mixture of hydrogen bromide salts of bis-(beta-dichlorethyl)-hydrazides of cystine and cysteine, respectively, in which each component in the composition varies within the range of 1 to 99 weight percent.

2. Method for the suppression of transplanted tumors in animals by administering thereto an effective amount for suppressing transplanted tumors of a mixture of hydrogen bromide salts of bis-(beta-dichloroethyl)-hydrazides of cystine and cysteine, respectively, in which each component in the composition varies within the range of 1 to 99 weight percent.

3. A method for the suppression of transplanted tumors in animals by administration to an animal having a transplanted tumor of an effective amount for suppressing transplanted tumors a mixture of hydrogen bromide salts of bis-(beta-dichloroethyl)-hydrazides of cystine (I) and cysteine (II) at a composition ratio of I:II of 95:5.

* * * * *